United States Patent [19]

Pfeiler et al.

[11] Patent Number: 5,042,486

[45] Date of Patent: Aug. 27, 1991

[54] CATHETER LOCATABLE WITH NON-IONIZING FIELD AND METHOD FOR LOCATING SAME

[75] Inventors: Manfred Pfeiler, Erlangen; Helmut Ermert, Roettenbach, both of Fed. Rep. of Germany

[73] Assignee: Siemens Aktiengesellschaft, Munich

[21] Appl. No.: 581,556

[22] Filed: Sep. 12, 1990

[30] Foreign Application Priority Data

Sep. 29, 1989 [EP] European Pat. Off. ........ 89118096.0

[51] Int. Cl.$^5$ .............................................. A61B 5/06
[52] U.S. Cl. .................................. 128/653 R; 128/658
[58] Field of Search ................. 128/653 R, 656, 658, 128/659, 662.02, 662.03, 662.06, 898

[56] References Cited

U.S. PATENT DOCUMENTS

| | | | |
|---|---|---|---|
| 3,847,157 | 11/1974 | Caillouette et al. | 128/653 R |
| 4,173,228 | 11/1979 | Van Steenwyk et al. | 128/653 R |
| 4,431,005 | 2/1984 | McCormick | 128/653 R |
| 4,697,595 | 10/1987 | Breyer et al. | |
| 4,905,698 | 3/1990 | Strohl et al. | 128/653 R |
| 4,989,608 | 2/1991 | Ratner | 128/653 R |

FOREIGN PATENT DOCUMENTS 0091577 10/1983 European Pat. Off. .
2545349 11/1984 France .

OTHER PUBLICATIONS

"Ultrasonically Marked Catheter-A Method for Positive Echographic Catheter Position Identification", Breyer et al., Medical and Biological Engineering and Computing, vol. 22, No. 3 (1984), pp. 268-271.

Primary Examiner—Ruth S. Smith
Attorney, Agent, or Firm—Hill, Van Santen, Steadman & Simpson

[57] ABSTRACT

A catheter locatable with a non-ionizing field, such as an electromagnetic or acoustic field, has a transmitting or receiving antenna for the relevant field at its tip. Receiving or transmitting antennas for the non-ionizing field are attached to a patient in which the catheter is disposed. A receiver or transmitter is connected to these antennas, and converts the received field waves into electrical locating or image signals. The location of the catheter tip is then portrayed on a display combined with an image of the blood vessel structure acquired in a different manner, such as by x-ray imaging.

8 Claims, 2 Drawing Sheets

CATHETER LOCATABLE WITH NON-IONIZING FIELD AND METHOD FOR LOCATING SAME

BACKGROUND OF THE INVENTION

1. Field of the Invention

The present invention is directed to a catheter which can be located in a patient using a non-ionizing field, such as an electromagnetic or acoustic field, and to a method for locating such a catheter.

2. Description of the Prior Art

In angiographic examinations, and in particular in those using invasive techniques, a so-called pathfinder illustration is frequently used in combination with an x-ray transillumination. For identifying the exact topology of a vessel region of interest (vessel structure or vessel architecture) using a contrast agent, the x-ray image of the vessel structure is first acquired and stored. In the subsequent employment of a catheter, the catheter is portrayed in the transillumination images in which the vessels are not visible. The transillumination image sequences which reproduce the position, orientation and movement of the catheter are thus constantly combined (superimposed) with the contrast agent image which contains the vessel structure. The resulting overall sequences accordingly show the catheter within the vessel architecture, and thus allow a controlled motion by the physician.

This technique requires the use of a transillumination means both in the contrast agent injection for generating the stored image of the vessel architecture, and during the subsequent catheter employment. This means the patient and the physician must be subjected to a radiation exposure beyond that which would be required only for producing the stored image of the vessel architecture.

There is no reasonable substitute for the use of x-ray imaging with a contrast agent via a catheter for acquiring and storing images of the vessel architecture. The exposure ensues once, before the subsequent catheter employment. Such imaging requires only a low radiation exposure for the patient and the physician.

SUMMARY OF THE INVENTION

It is an object of the present invention to provide an alternative method for the permanent portrayal of the catheter during treatment by a method making use of non-ionizing rays, waves or fields, and thus having the advantage of limiting the radiation exposure for the patient and the physician.

It is a further object of the present invention to provide a catheter which can be locatable using such a non-ionizing field.

The above objects are achieved in a method for real-time portrayal of a catheter in a vessel, which makes use of a transmitter for electromagnetic or acoustic waves located at the tip of a catheter, these waves being acquired by a receiving antenna attached to the patient and being converted into electrical image signals. The image of the catheter is then superimposed on a radiologically-acquired vessel image. In an alternative embodiment, the catheter tip may be a receiving antenna, and the externally applied antennas may be transmitting antennas.

A catheter which can be located in a patient using an ultrasound transmitter allocated to the catheter is disclosed in U.S. Pat. No. 4,697,595 and in the technical note "ultrasonically marked catheter, a method for positive echographic catheter position identification," Breyer et al., Medical and Biological Engineering and Computing, May, 1984, pp. 268-271. There is no discussion in either of these references as to the superimposition of an image of the catheter produced in this manner with other images, particularly with a radiologically acquired vessel image.

The aforementioned known technology permits a simple portrayal of the catheter, because the catheter differs greatly from its environment (biological tissue) with respect to the interaction of x-rays. The pathfinder technique can be employed with an imaging method and with a corresponding, real-time imaging system which makes use of non-ionizing radiation, and which comparable or better contrast conditions are present, such as by using an ultrasound or microwave field. The non-x-ray image which portrays the catheter is combined with a contrast agent image in an appropriate way. The problem of excess radiation exposure is thus overcome, however, the demands made on the non-ionizing imaging system with respect to its applicability and resolution are rather high.

A further possibility, therefore, is to use the non-ionizing field as part of a locating method, as opposed to an imaging method. Locating methods differ from imaging methods in the following ways. Imaging methods are primarily used to topically correctly portray and resolve a number of subjects or subject points within an image, within specific limits. This property is known as the multi-target capability in radar technology, and is not present in locating methods. Locating methods operate precisely and unambiguously only in the case wherein a single subject is to be portrayed, i.e. to be located. A catheter is actually not a single target, however, its complete imaging requires a suitable, multi-target-capable imaging method. Due to the availability of the topographical portrayal of the vessel architecture, however, the given direction of movement of the catheter is known in conventional pathfinder technology. If one then succeeds in permanently locating a singular and suitable subject point, for example, the tip of the catheter, in storing successive positions, and thus also tracking the movement of this point, all of the information is then available which is necessary for a reconstruction and visual portrayal of the catheter in the underlying contrast agent image. The advantage of the locating method is that wave fields can be used wherein the employed wavelength, which is defined by the frequency and phase velocity of the surrounding medium (tissue), can be relatively high, and need not be on the order of magnitude of the locating precision. As is known, range decreases greatly with increasing frequency given non-ionizing waves, such as electromagnetic waves and acoustic waves.

It is thus possible, given the use of a locating method, to make use of relatively long wavelengths, and thus lower frequencies. Moreover, the outlay for signal bandwidth and aperture is much smaller in locating methods than in imaging methods, particularly in view of the spectral (signal) and spatial (aperture) occupation density. It is sufficient to bring the subject point to be located into interaction with only a few extracorporeal aperture support points, for example, three to five transmitters or receiver, given a few discreet frequencies, for example three to five frequencies. On the basis of this interaction, ranges or range differences with reference to the subject position and the various aperture supporting points, the combination of which makes an unambiguous and exact positional identification (locating) of the subject point possible, are determined by measuring phase relationships or transit time relationships. The subject point, i.e. the catheter tip, must be marked for this purpose in a suitable manner. As in conventional pathfinder technology, it is necessary that the catheter image and the vessel image be combined with each other in a proper three-dimensional correspondence, and it is also necessary that the vessel architecture does not displace or deform during the treatment.

The above principles can be applied for examining other cavity structures of the body, for example to the gall duct system, and for regions having structures which yield an orientation image by their contrast behavior, for example, bones. Dependent on the examination technique, the catheter may be replaced by a needle whose tip is to be located.

The following technical realizations are achievable with the method disclosed herein.

For locating using electromagnetic fields, marking of the catheter tip is achieved by an antenna disposed at the catheter tip, with an antenna feed guided in or along the catheter. An electrical antenna (dipole) or a magnetic antenna (loop) can be used. An advantage of these antenna types is that their polarization properties make locating an identification of the orientation of the catheter tip possible. The antenna can be operated as a transmission antenna or as a reception antenna, with the extracorporeal antennas located at the skin surface correspondingly functioning as reception antennas or transmission antennas. Given multi-path propagation between the catheter tip and the external antennas, the direct, i.e. shortest, path between the relevant antennas can be calculated by a suitable multi-frequency or broadband technique. Due to the relatively large dielectric inhomogeneity of the biological tissue, an unassisted locating with this method will not be very exact. If, however, the current position of the catheter tip is made briefly available at a time, or at a number of times, for example by transillumination, relative changes in the position in the following time or in the chronological spaces can be identified with great precision with the electromagnetic locating method. It is also possible to employ the locating method using acoustic waves. The problem of the contrast of the biological tissue is significantly less critical when acoustic waves are used than in the electromagnetic embodiment. The problem of multi-path propagation in the case of acoustic waves, however, will be greater for this embodiment because of the lower attenuation offered by the biological tissue. Both problems, however, can be solved in the same manner as described above in connection with the electromagnetic embodiment. The possibility of defining the orientation of the catheter tip is not possible in the acoustic embodiment, as in the electromagnetic embodiment, because acoustic waves lack a polarization property. Pronounced directional characteristics of the acoustic antennas, however, can be used for identifying the orientation of the catheter tip as the carrier for the antenna. Providing the catheter tip with a plurality of separate antenna elements offers a further possibility for identifying the orientation.

A ceramic or polymeric piezoelectric element can be used as the antenna at the catheter. Due to the high transmission signal amplitudes, operation of the catheter antenna as a reception antenna is preferred for the case of acoustic locating. Because the transmission paths are reciprocal relative to each other, the locating results are equivalent given reversal of the transmission direction.

DESCRIPTION OF THE PREFERRED EMBODIMENTS

Figure 1:
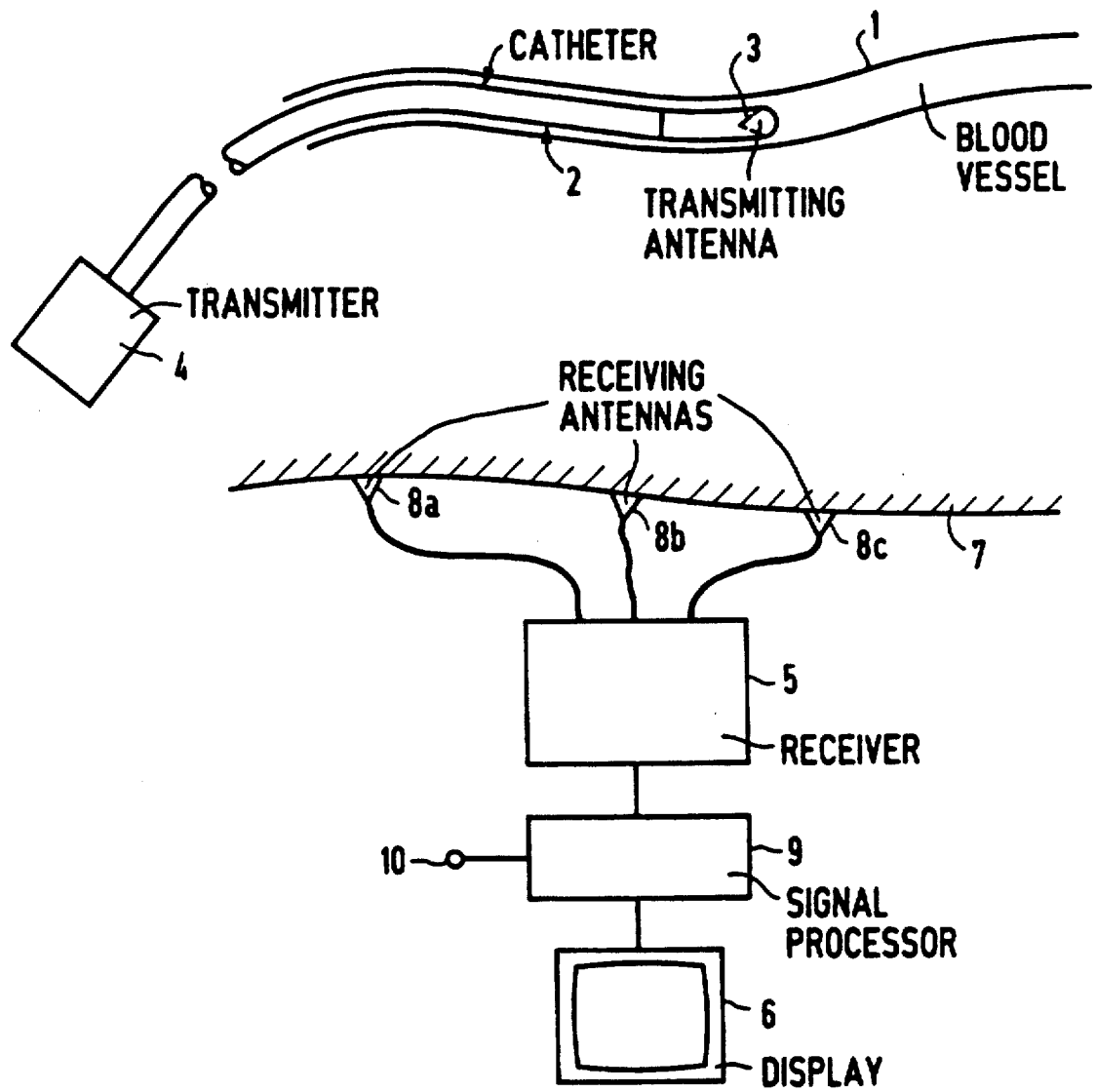
FIG. 1 is a schematic block diagram for illustrating the locating method in accordance with the principles of the present invention making use of a transmitting antenna at the catheter tip.

As shown in FIG. 1, a catheter 2 is introduced into a vessel 1 in the body of a patient. The catheter 2 has an antenna 3 at its tip, which is supplied with energy by a transmitter 4. The transmitting antenna 3 may be, for example, a dipole.

A receiver 5 is provided for locating the position of the tip 3. A receiver 5 receives the electromagnetic waves generated by the antenna 3 by means of a plurality of receiving antenna 8a, 8b and 8c placed on the body surface 7 of the patient. A display 6 permits visual portrayal of the position of the catheter tip as described earlier, for example, by superimposition with an x-ray showing the vessel architecture.

The signals from the receiver 5 are supplied to a signal processor 9 which constructs an image of the catheter. Information regarding the vessel architecture are supplied to the signal processor 9 via a separate input 10. The images are superimposed and are portrayed on the display 6.

As noted above, the transmitter and receiver may be an ultrasound transmitter or receiver, instead of electromagnetically operating devices.

Figure 2:
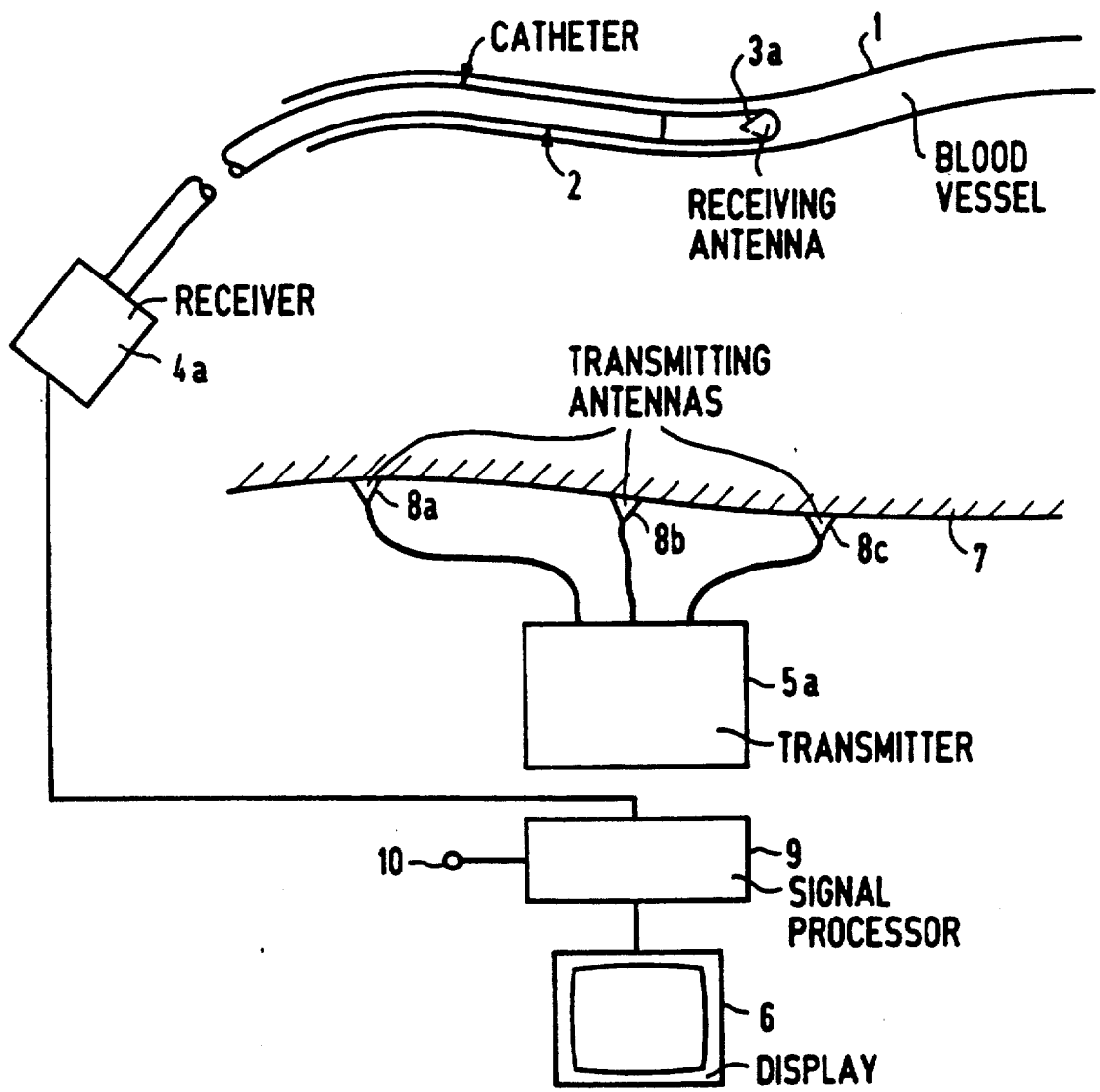
FIG. 2 is a schematic block diagram for illustrating a second embodiment in accordance with the principles of the present invention using a receiving antenna at the catheter tip.

An alternative embodiment is shown in FIG. 2, wherein the antenna 3a is a receiving antenna. In this embodiment, the antenna 3a is connected to a receiver 4a, and the antennas 8a, 8b and 8c located at the body surface 7 are transmitting antennas. The transmitter 5a transmits signals to the transmitting antennas 8a, 8b, and 8c. Operation of the method is otherwise identical to that described in connection with FIG. 1. The embodiment of FIG. 2 can be operated as well using acoustic transmission and reception components instead of electromagnetic transmission and reception components.

In all of the above embodiments, a continuous image of the catheter tip is generated, with the positions located in the chronological sequence describing the path the catheter tip has traversed. The region of the tip can be provided with individually locatable segments, as indicated by the dashed lines indicating the antenna 3 in both embodiments. This permits the location and the direction of the catheter tip to be identified using a multi-frequency or a multiplexing method.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for real-time locating of a catheter in a vessel in a patient comprising the steps of:
   obtaining a radiological vessel image;

obtaining an image using ionizing radiation of a catheter in a vessel contained within said vessel image using a non-ionizing field; and superimposing said image of said catheter on said radiological vessel image.

2. A method as claimed in claim 1 wherein the step of obtaining an image of said catheter using a non-ionizing field is further defined by obtaining an image of a tip of said catheter using said non-ionizing field.

3. A method as claimed in claim 1 wherein the step of obtaining an image of said catheter using a non-ionizing field is further defined by the steps of:

operating an antenna disposed at a tip of said catheter as a transmitting antenna for non-ionizing field signals;

receiving the non-ionizing field signals from said transmitting antenna by a plurality of receiving antennas disposed externally at a surface of said patient; and converting the received signals into electrical image signals for generating an image of said catheter tip.

4. A method as claimed in claim 1 wherein the step of obtaining an image of said catheter using a non-ionizing field is further defined by the steps of:

operating an antenna disposed at a tip of said catheter as a receiving antenna for non-ionizing field signals;

transmitting the non-ionizing field signals to said receiving antenna from a plurality of transmitting antennas disposed externally at a surface of said patient; and converting the received signals into electrical image signals for generating an image of said catheter tip.

5. A method as claimed in claim 1 wherein the step of obtaining an image of said catheter using a non-ionizing field is further defined by obtaining an image of said catheter using an electromagnetic field.

6. A method as claimed in claim 1 wherein the step of obtaining an image of said catheter using a non-ionizing field is further defined by obtaining an image of said catheter using an acoustic field.

7. A method as claimed in claim 1 wherein the step of obtaining an image of said catheter using a non-ionizing field as further defined by the step of:

locating the successive positions of said catheter in a chronological sequence to describe a continuous image of the path which the tip of said catheter has traversed.

8. A method as claimed in claim 1 comprising the additional steps of:

providing said catheter with a plurality of individually locatable segments; and identifying the location and direction of a tip of said catheter using said locatable segments.

* * * * *

UNITED STATES PATENT AND TRADEMARK OFFICE
CERTIFICATE OF CORRECTION

PATENT NO. : 5,042,486
DATED : August 27, 1991
INVENTOR(S) : Manfred Pfeiler and Helmut Ermert It is certified that error appears in the above-indentified patent and that said Letters Patent is hereby corrected as shown below:

In Column 4, line 68, after "image" and before ";", insert —using ionizing radiation—.

In Column 5, line 1, delete "using ionizing radiation".

Signed and Sealed this

Twenty-fourth Day of September, 1996

Attest:

BRUCE LEHMAN

Attesting Officer     Commissioner of Patents and Trademarks